(12) United States Patent
Jackson

(10) Patent No.: US 6,193,703 B1
(45) Date of Patent: *Feb. 27, 2001

(54) ADJUSTABLE SCROLL ABSORBENT ARTICLE AND METHOD

(75) Inventor: Wanda W. Jackson, Alpharetta, GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/079,471

(22) Filed: May 15, 1998

(51) Int. Cl.[7] ..................................................... A61F 13/15
(52) U.S. Cl. ..................................... 604/385.04; 604/387
(58) Field of Search ..................................... 604/387, 386, 604/385.1, 389, 383, 385.04

(56) References Cited

U.S. PATENT DOCUMENTS

| | | |
|---|---|---|
| 4,917,697 | 4/1990 | Osborn, III et al. . |
| 5,037,418 | 8/1991 | Kons et al. . |
| 5,087,254 | 2/1992 | Davis et al. . |
| 5,154,715 | 10/1992 | Van Iten . |
| 5,221,275 | 6/1993 | Van Iten . |
| 5,558,663 | 9/1996 | Weinberger et al. . |
| 5,584,829 | 12/1996 | Lavash et al. . |
| 5,591,147 | 1/1997 | Couture-Dorschner et al. . |
| 5,591,150 | 1/1997 | Olsen et al. . |
| 5,611,879 | 3/1997 | Morman . |
| 5,615,691 | 4/1997 | Huffman . |
| 5,624,425 | 4/1997 | Gray et al. . |
| 5,628,739 | 5/1997 | Hsieh et al. . |
| 5,643,653 | 7/1997 | Griesbach, III et al. . |
| 5,650,223 | 7/1997 | Weinberger et al. . |
| 5,704,930 | 1/1998 | Lavash et al. . |
| 5,713,885 | * 2/1998 | Jorgenson et al. ................. 604/385.2 |
| 5,755,711 | * 5/1998 | Hammons et al. ................. 604/385.1 |

FOREIGN PATENT DOCUMENTS

| | | |
|---|---|---|
| 0651986 | 5/1995 | (EP) . |
| 9623469 | 8/1996 | (WO) . |

* cited by examiner

Primary Examiner—Dennis Ruhl
(74) Attorney, Agent, or Firm—Thomas J. Connelly; Thomas M. Parker; Douglas G. Glantz

(57) ABSTRACT

An absorbent article and method are disclosed for providing side leakage protection for an undergarment and absorbent article positioning guidance for proper placement on the undergarment. An absorbent configured to fit the pudendal region of a woman and a liquid-impermeable baffle are provided with a pair of garment-attachment adjustable scroll members for receiving an arcuately shaped crotch portion of an undergarment. Arcuately shaped curled folds on a lateral side surface of the absorbent article form the adjustable scroll members. In one aspect, the arcuately shaped curled folds are formed in a layer of polyethylene/polypropylene bi-component web sheet material. In one aspect, the arcuately shaped curled folds include a liquid impervious backing.

3 Claims, 3 Drawing Sheets

ADJUSTABLE SCROLL ABSORBENT ARTICLE AND METHOD

BACKGROUND OF THE INVENTION

1 Field of the Invention

This invention relates to an absorbent article and method for protecting a user by absorbing or containing body fluids including menstrual fluids and/or other body exudates. More specifically, this invention relates to an absorbent article and method having side leakage protection and novel means and method for positioning and fastening the absorbent article to an undergarment.

2. Background of the Invention

Currently, wide varieties of products for the absorption of human body fluids are available in the form of feminine pads, sanitary napkins, panty shields, panty liners, and incontinence devices. Absorbent products for providing feminine care sanitary protection are designed to absorb body fluids, including menses, and come in different functional designs. Sanitary napkins and feminine pads externally worn about the pudendal area are absorbent pads designed primarily for menstrual flow. Panty liners or panty shields are thin sanitary napkin products worn about the pudendal area for light menstrual flow. Absorbent products for providing incontinence protection are designed to absorb body fluids, including urine.

These absorbent products generally have an absorbent positioned between a liquid-permeable body-side cover and a liquid-impermeable garment-facing baffle. These absorbent products include a top layer of the liquid-permeable body-side cover, a middle layer of the absorbent, and a bottom layer of the liquid-impermeable garment-facing baffle. A pressure sensitive adhesive generally is secured to the baffle. The pressure sensitive adhesive is used to attach the product to an inner crotch portion of an undergarment.

INTRODUCTION TO THE INVENTION

While absorbent products are commercially available and used widely today, a problem of leakage still persists, in that body fluids leak out at the sides of the absorbent products. Such side leakage can stain the undergarment and even the outer garments of a wearer, and accordingly such side leakage is a serious concern of the absorbent product user.

Side flaps, tabs, wings, and other side constructions, which extend from the sides of a feminine care pad, herein after are referred to as "side flaps." Side flaps have been designed to fold onto opposite side flaps or to wrap around the undergarment to provide protection from side leakage. While side flaps available today have some success in absorbing side leakage, such side flaps have certain drawbacks.

Side flaps available today are costly to manufacture as they require non-conforming shapes creating excessive trim waste.

Side flaps available today also are awkward to use. Such side flaps require careful placement within the crotch portion of the wearer's undergarment, and even then are not generally comfortable to the wearer. Side flaps typically do not maintain their position when the protective adhesive peel strip is removed from the garment-facing side of the side flaps. Many times, the side flaps then become adhered to the garment side of the baffle, or they become inadvertently and undesirably adhered or stuck to another inappropriate surface. The user then must manipulate the side flap sticking to the baffle or other inappropriate surfaces, so as to guide and position the side flaps into proper positioning prior to use. The inadvertent sticking of the side flap to the baffle or other inappropriate surfaces many times makes the article unusable. Releasing the absorbent article product from the undergarment also can be difficult and inconvenient.

Another drawback of side flaps available today has been found when the wearer has only a light menstrual flow and does not need the side flaps. In these situations, many customers prefer not to use the side flaps during light menstrual flow because of their many drawbacks.

Many absorbent products available commercially today generally are designed to be attached to an adjacent undergarment, and they should be designed to be held stationary during use. Absorbent products, such as sanitary napkins, overnight pads, panty liners, incontinent garments, and even some underarm shields, are attached to an adjacent garment or undergarment for positioning and support. Pressure sensitive adhesives typically provide the means and method for affixing the absorbent product to an adjacent garment or undergarment. The pressure sensitive adhesive normally is applied to the garment-facing surface of the absorbent product and is covered temporarily by a releasable peel strip until the absorbent product is placed into use.

Pressure sensitive adhesive as applied to the garment-facing surface of the absorbent product is widely used in commercially available products today, but certain drawbacks have been found to persist. The cost of the adhesive and the cost of the releasable peel strip increase the overall cost of the absorbent product. Also, special equipment and extra steps are required during the manufacturing of absorbent products to apply the pressure sensitive adhesive and then to center and apply the releasable peel strip over the adhesive. The adhesive also can be a nuisance when it sticks to the inner surface of an undergarment, and when it leaves a tacky residue after the absorbent product is removed. The tacky residue is uncomfortable to the wearer, and the build up of the tacky residue produces a stain and eventually may ruin the undergarment. Further drawbacks are found in that it is difficult to reposition the absorbent product in the undergarment, e.g., in the manner of repositioning side flaps, after the adhesive has been attached to an inappropriate surface of the undergarment or other inappropriate surface.

Accordingly, there is a need for an absorbent article and method which provide side leakage protection, which prevent staining of undergarments and outer garments, and which provide a lower cost to produce the absorbent article, with lower manufacturing costs and lower material production. costs. An absorbent article and method also are needed which provide accurate positioning and convenient placement of the absorbent article onto the undergarment. An absorbent article and method also are needed which provide the user with a sense of comfort during use over a variety of situations, including in one aspect, when full absorbency is not needed, yet without sacrificing the full benefits of full leakage protection, convenience of positioning and application, and wearer comfort.

SUMMARY OF THE INVENTION

Briefly, the present invention provides an absorbent article and method for protecting an undergarment from side leakage and for guiding the absorbent article into position for proper placement on the undergarment. An absorbent configured to fit the pudendal region of a woman and a liquid-impermeable baffle are provided with a pair of garment-attachment adjustable scroll members for receiving an arcuately shaped crotch portion of an undergarment.

Arcuately shaped curled folds on a lateral side surface of the liquid-impermeable baffle form the adjustable scroll members. In one aspect, a liquid impervious backing surface is provided on each adjustable scroll member which does not readily wick fluid so that the fluid is immobilized in a local area. In one aspect, the arcuately shaped curled folds are formed by a polyethylene/polypropylene bi-component web material.

The article and method of the present invention include providing an absorbent designed to be attached to a crotch portion of an undergarment and having a body-side surface and an opposite garment-facing surface. A liquid-impermeable baffle is positioned adjacent to at least a portion of the garment-facing surface of the absorbent, and a liquid-permeable cover is positioned adjacent to at least a portion of the body-side surface of the absorbent. The cover and baffle cooperate to enclose the absorbent and form a pad having a pair of longitudinally oriented side edges and a pair of distally spaced ends. A garment-adhesive strip is secured to the garment-facing surface of the pad and is positioned along a longitudinal axis of the pad. Two adjustable scroll members are positioned along the longitudinal axis of the pad and are configured to provide positioning guidance and support to the wearer for placing and holding the absorbent onto the undergarment. The adjustable scroll members are configured to prevent staining of the crotch portion of the undergarment or an outer garment. In one aspect, a liquid impervious backing surface is provided on the adjustable scroll member. The adjustable scroll members accommodate varying crotch widths of the undergarment.

In one aspect, the absorbent article of the present invention includes an absorbent having a first sheet surface and an opposite second sheet surface, the first sheet surface having a length and a width configured to fit the pudendal region of a woman. A liquid-permeable cover is secured to the first sheet surface. A liquid-impermeable baffle is secured to the second sheet surface, the baffle having a length and a width covering the second sheet surface. A means for garment attachment includes a garment-attachment adhesive for securing the liquid-impermeable baffle to an inside surface of a crotch of an undergarment and a releasable peel strip covering the garment-attachment adhesive. Adjustable scroll members on the side of the absorbent article are formed of curled folds positioned to guide the absorbent article into proper placement on a wearer's undergarment and hold the absorbent article in proper position on a wearer's undergarment during use.

A method of positioning and holding an absorbent article includes the steps of providing an absorbent article having an absorbent and a liquid-impermeable baffle, the absorbent having a length and a width configured to fit the pudendal region of a woman, and positioning the absorbent article onto an undergarment by placing a crotch portion of the undergarment into a pair of adjustable scroll members formed on the side of the absorbent article. The adjustable scroll members are formed from curled folds positioned on the lateral sides of the absorbent article.

A general object of the present invention is to provide an absorbent article capable of absorbing and containing menstrual fluids and/or other body exudates.

It is an object of the present invention to provide an absorbent article and method for protecting the undergarment of a wearer from side leakage.

It is another object of the present invention to provide an absorbent article and method for guiding the absorbent article into proper placement onto the undergarment of a wearer.

A more specific object of this invention is to provide an absorbent article and method for holding the absorbent article in proper position on the undergarment of a wearer.

Another object of the present invention is to provide a sanitary napkin or panty liner or panty shield having manufacturing cost advantages.

It is an object of the present invention to provide a sanitary napkin or panty liner or panty shield having cost of material advantages.

A further object of the present invention is to provide a sanitary napkin or panty liner or panty shield which uses less material.

It is an object of the present invention to provide an absorbent article which is more convenient to use.

It is an object of the present invention to provide an absorbent article which is more comfortable to wear.

These and other objects and advantages of the present invention will become more apparent to those skilled in the art in view of the following detailed description and the accompanying drawings.

DETAILED DESCRIPTION OF THE PREFERRED EMBODIMENTS

Figure 1:
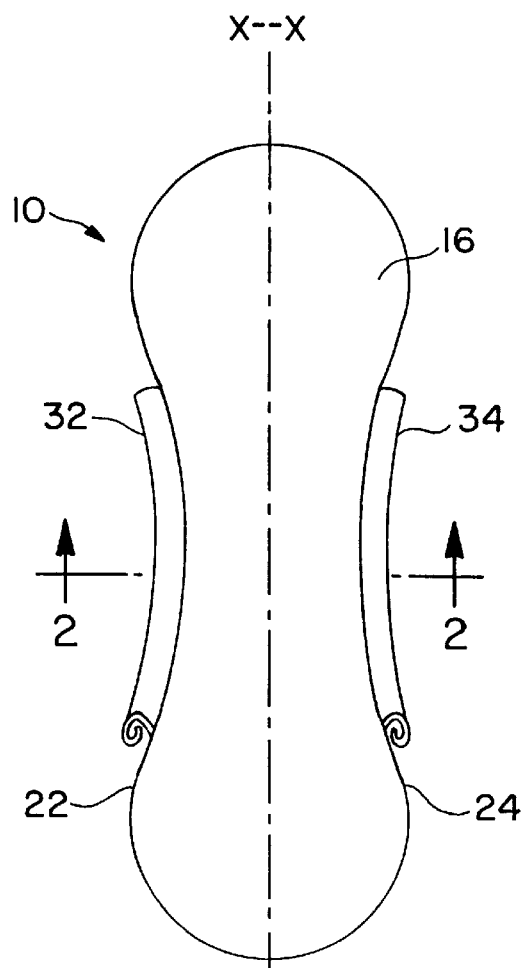
FIG. 1 is a top view of an absorbent article of the present invention.
Figure 2:
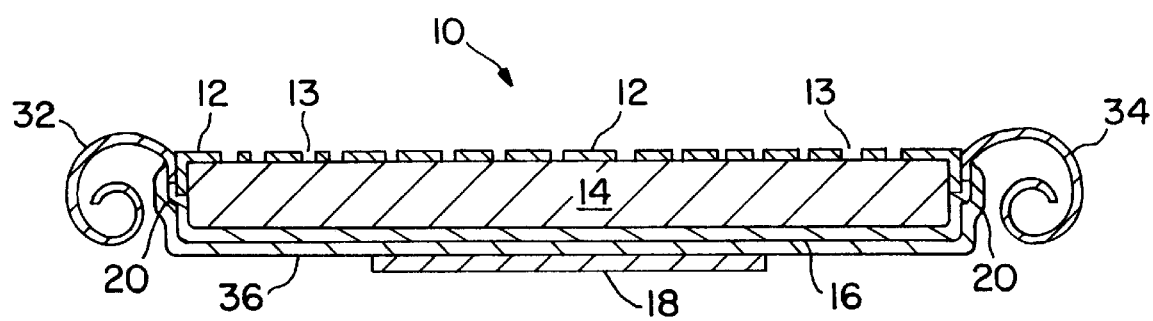
FIG. 2 is a cross sectional view, taken along line 2—2 of FIG. 1, of an absorbent article of the present invention.

Referring now to FIGS. 1 and 2, an absorbent article 10 is shown as a feminine care sanitary napkin. The article and method of the present invention also have application to other absorbent article embodiments, such as a panty liner or a panty shield, an incontinent garment, a urinary shield, or an underarm pad. For purposes of illustration, the absorbent article 10 will be described as a sanitary napkin or feminine care sanitary protection pad.

The absorbent article 10 is depicted having a liquid-permeable cover 12, an absorbent 14, and a liquid-impermeable baffle 16. The absorbent 14 is positioned between the liquid-permeable cover 12 and the liquid-impermeable baffle 16. The absorbent article 10 is constructed to form layers of the liquid-permeable cover 12, the absorbent 14, and the liquid-impermeable baffle 16, vertically arranged.

The liquid-permeable cover 12 is made of a material designed to serve functionally as the material which will come into contact with a wearer's body. The liquid-permeable cover 12 is made from a woven or non-woven, natural or synthetic material which is readily penetrated by body fluids. Thermoplastic polymer films made from fibers or filaments of polyethylene or polypropylene are preferred for cover 12.

Cover 12 has apertures 13 formed in the cover 12 to increase the rate at which the body fluids penetrate through the cover 12 into the absorbent 14.

The absorbent 14 is hydrophilic and is made of cellulose fibers, wood pulp, regenerated cellulose, cotton fibers, or a blend of pulp and other fibers. The absorbent 14 usually is resilient for enabling the absorbent article 10 to bend easily without excessive distortion. Hydro colloidal material, commonly referred to as super absorbents, can be added to the hydrophilic material to increase the absorption capacity of the absorbent article 10.

The absorbent article 10 provides service as a sanitary napkin, a panty liner, or a panty shield pad, and comes into attachment to the inside surface of a crotch portion of an undergarment. The undergarment most often is a fabric panty having an elastic waist and leg openings separated by fabric material defining the crotch. The liquid-impermeable baffle 16 of the absorbent article 10 faces the inner surface of the crotch portion of the undergarment and can be designed to permit the passage of air or vapor out of the absorbent article 10 while blocking the passage of body fluid.

The baffle 16 can be made from a polymeric film such as polyethylene, polypropylene, or cellophane, or can be made from a bi-component film. One such material is ethyl-vinyl-acetate/polyethylene co-extruded film. In one aspect, the baffle 14 can be constructed from a liquid-permeable material that has been treated or coated to become liquid-impervious.

The cover 12 and the baffle 16 can be attached or joined together, such as by a peripheral seal 20, to enclose the absorbent 14. The cover 12 can be wrapped entirely about the absorbent 14, and then the baffle 16 can be attached to the lower surface of the cover 12 by end seals (not shown).

The absorbent article 10 usually has an overall length of between about 6 to 12 inches (15 to 30 cm) and a width of between about 2 to 3.5 inches (5 to 9 cm), sometimes about 1.5 to 3.5 inches (4 to 9 cm). The thickness of absorbent article 10 can vary form about 2 mm to about one inch (2.5 cm).

The absorbent article 10 has a first side 22 and a second side 24 longitudinally extending along a longitudinal axis X-X of the absorbent article 10. The first side 22 is situated on one side of the absorbent article 10 width as viewed relative to the longitudinal axis X-X, and the second side 24 is situated on the other side of the width of the absorbent article 10, opposite to the first side 22.

The first side 22 and the second side 24 of the absorbent article 10 have a curled fold or scroll 32 and a curled fold or scroll 34, respectively, positioned and extending along the length of absorbent article 10.

Scroll 32 and scroll 34 provide a curled fold or adjustable scroll member for garment attachment to a lower surface 36 of the absorbent article 10. In one aspect, scroll 32 and scroll 34 can be made to be a part of the baffle 16.

Figure 3:
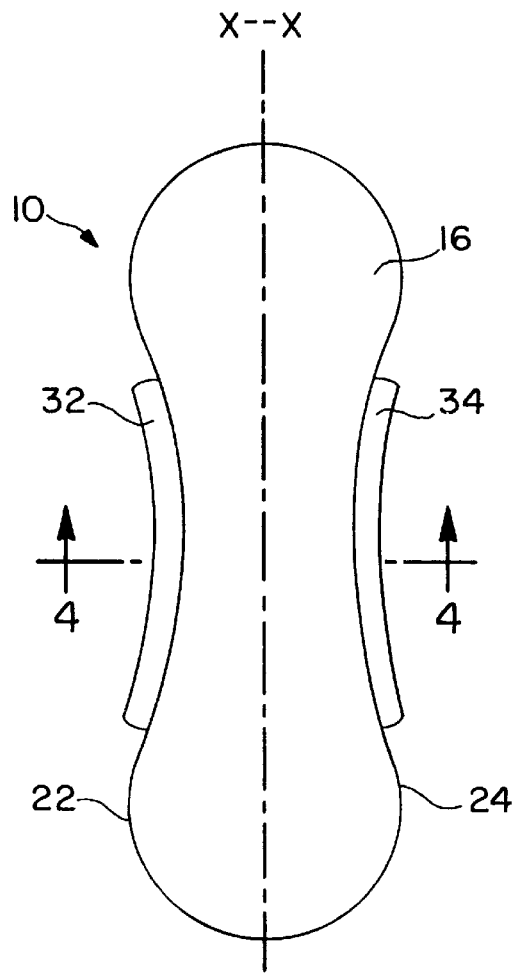
FIG. 3 is a top view of an absorbent article of the present invention attached to a crotch portion of an undergarment.
Figure 4:
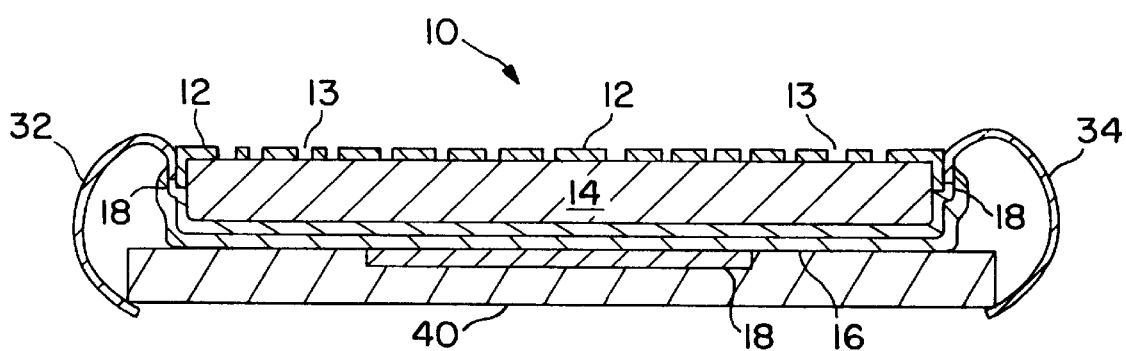
FIG. 4 is a cross sectional view, taken along line 4—4 of FIG. 3, of an absorbent article of the present invention attached to a crotch portion of an undergarment.

Referring now to FIGS. 3 and 4, the absorbent article 10 is shown attached to an undergarment 40.

The scroll 32 and the scroll 34 provide an adjustable nesting groove or adjustable scroll member formed by curled folds created on the sides of absorbent article 10 and extending to an underside of absorbent article 10. The folds of scroll 32 and scroll 34 are grooves or curves where a crotch portion of an undergarment 40 may nest in a manner to be protected from body fluid staining.

When the absorbent article 10 is positioned in the crotch portion of the undergarment 40, the wearer simply allows the undergarment 40 to insert into scroll 32 on one side, and into scroll 34 on the other side, of the absorbent article 10. The wearer then pulls the undergarment 40 up about her torso, and the absorbent article 10 will contact and conform to her body. The body forces exerted on the absorbent article 10 operate to force or to nest the undergarment 40 into scroll 32 on one side, and into scroll 34 on the other side, of the absorbent article 10.

The adjustable scroll members 32 and 34 are arcuately shaped to conform to the arcuate shape of an undergarment 40, such as the arcuate shape of the side of crotch portion of a panty. In another embodiment, the adjustable scroll members of the present invention can be linear rather than arcuately shaped.

The adjustable scroll members of the absorbent article of the present invention include curled folds formed on a thin layer of bicomponent web material laminated to the baffle of the absorbent article of the present invention. Alternatively, the adjustable scroll members of the absorbent article of the present invention include curled folds formed from a sheet of a one-sided stretch laminate which automatically curls along a cut edge. An elastomeric film on one side of the laminate and a non-woven fabric on an opposite side of the laminate are laminated in a tension or stretch state. When relaxed, the film side relaxes more than the non-woven side which causes the laminate to retract more.

Figure 5:
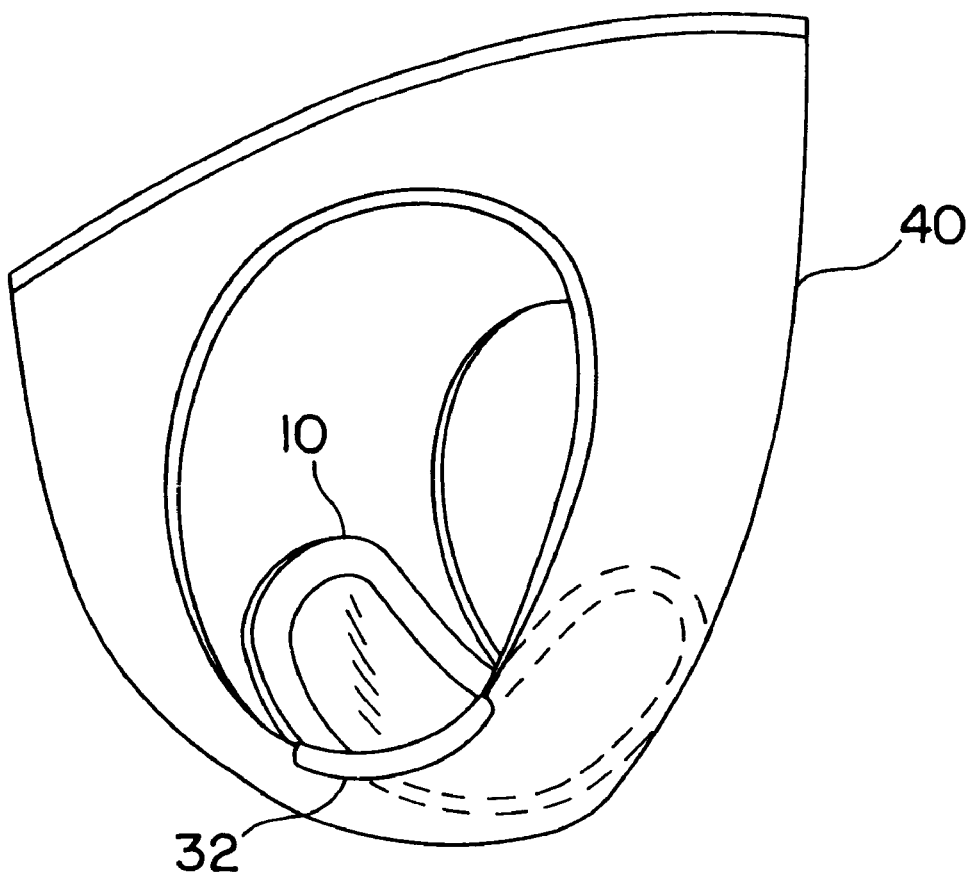
FIG. 5 is a perspective view of an absorbent article of the present invention attached to a crotch portion of an undergarment.

Referring now to FIG. 5, an absorbent article 10 is shown attached to an undergarment 40. A scroll 32 and a scroll 34 provide an adjustable nesting member formed by curled folds created on the sides of absorbent article 10 and extending to an underside of absorbent article 10 and around an undergarment 40.

When the absorbent article 10 is positioned in the crotch portion of the undergarment 40, the wearer simply allows the undergarment 40 to insert into scroll 32 on one side, and into scroll 34 on the other side, of the absorbent article 10. The wearer then pulls the undergarment 40 up about her torso, and the absorbent article 10 will contact and conform to her body. The body forces exerted on the absorbent article 10 operate to force or to nest the undergarment 40 into scroll 32 on one side, and into scroll 34 on the other side, of the absorbent article 10.

The absorbent article and method of the present invention provide sanitary protection wherein each side edge 22 and 24 of the absorbent article 10 has a scrolled or curled fold edge component 32 and 34, respectively, capable of wrapping around the side leg elastic of undergarment 40 and protecting undergarment 40 from staining. The scroll members 32 and 34 also guide the undergarment 40 into proper placement with absorbent article 10 and hold undergarment 40 in proper position. The scroll members 32 and 34 are unfurled to various degrees to accommodate crotches of differing widths. The protective edges can be curved to conform to the contours of the absorbent article, e.g., such as a sanitary napkin pad, and to the contours of the body. The structure of absorbent article 10 is rigid enough to maintain its shape but is cushioned for comfort. The scrolled members 32 and 34 can be covered with material which will absorb small amounts of fluid and are backed with a barrier material.

A sanitary protection product, e.g., such as an ultra-thin panty liner, a thin panty shield, or a full size maxi-pad, having the scrolled material attached to its side edges has been found to protect the wearer's undergarment and further has been found to hold the sanitary protection product place. For example, a pad having a fluff absorbent, a fluid pervious cover, and a fluid impervious baffle has attached to each side a scrolled component, e.g., such as a curled fold thermal formed from bi-component spunbond material, extending along the center third of the pad, approximately. The bi-component spunbond material is curled outwardly, away from pad surface, and is wound several times onto itself. The bi-component spunbond material may be between 0.8 and 2.0 oz. per sq. yd. basis weight. Such a curled material is sufficiently stiff to maintain its shape but not so stiff as to be uncomfortable. The scrolls in the curled material are curved to conform to the contours of the pad edges and can unfurl to various degrees to accommodate different crotch widths but still provide the stain protection of the present invention. The bi-component spunbond material is absorbent enough to contain a small amount of fluid and is backed with a liquid impervious barrier material. The surface does not readily wick fluid so it is immobilized in a local area. Alternatively, the absorbent could be on the upward facing surface only.

These scrolled edges of the present invention are confined to the crotch area of the pad. In one embodiment, the scrolled edges of the present invention extend the entire length of the pad. In another embodiment, the scrolled edges of the present invention can have breaks to allow various crotch sizes and shapes to reside where best fitting. The scrolled edges also hold the pad in place as they grip the panty elastic.

Baffle 16, in a preferred embodiment, is laminated to a polyethylene/polypropylene bi-component web material formed to provide curled folds 32 and 34 to provide the adjustable scroll member of the absorbent article of the present invention. The polyethylene/polypropylene bi-component web material is curled to form the folds forming the adjustable scroll member of the absorbent article of the present invention. The curled polyethylene/polypropylene bi-component web material baffle then is put in an oven at about 265 degrees Fahrenheit to set the curled folds 32 and 34. The curled folds 32 and 34 formed from the polyethylene/polypropylene bi-component web material have been found to be comfortable to the wearer when serving as the absorbent article of the present invention.

The adjustable scroll member of the absorbent article of the present invention must resist the force of the panty and stay curled. It is also important that the absorbent article of the present invention provide comfortable wear to the user.

In a preferred embodiment, the adjustable scroll members 32 and 34 of the absorbent article of the present invention resist the force of the panty and stay folded, provide comfortable wear to the user, and also include a friction-enhancing material, such as a latex or a rubberized material having a high co-efficient of friction, to reduce the sliding of the panty elastic or fabric in the adjustable scroll, thereby to reduce twisting and shifting of the undergarment.

The adjustable scroll members 32 and 34 of the absorbent article 10 of the present invention provide for the comfortable accommodation of various crotch widths of the undergarment 40.

The adjustable scroll members of the absorbent article of the present invention include curved folds which are contoured to follow the shape of a panty crotch so that the undergarment lies smooth with no bunching. The adjustable scroll members of the absorbent article of the present invention also assist in keeping the absorbent article in position during wear.

A garment adhesive 18 is placed in the center of the underside of the absorbent article of the present invention. In one embodiment, a small amount of adhesive is placed in the adjustable scroll member of the present invention for additional security in holding the panty.

In accordance with the article and method of the present invention, folds on the underside of the absorbent article of the present invention form scrolled, curled folds where the panty crotch fabric may nest, protected from staining.

In accordance with the article and method of the present invention, the panty elastic is placed between the folds of a adjustable scroll member on each side of the absorbent article of the present invention. In this way, the panty elastic and the crotch portion of the panty itself are held out of the way of body fluid contact. The panty crotch is gathered between the protective folds of the adjustable scroll members on the underside of the absorbent article of the present invention.

In accordance with the article and method of the present invention, the panty is automatically placed into position on the absorbent article of the present invention when it is placed between the folds of an adjustable scroll member on each side. The article and method of the present invention overcome the problems and drawbacks in respect to positioning of side flaps available commercially today, and in respect to positioning and repositioning an absorbent article attached and positioned by adhesive.

The present invention provides an article and method for guiding, positioning, and holding an absorbent pad in position on a wearer's undergarment, and protecting the undergarment from side leakage staining of body fluids. The method includes pulling the absorbent article of the present invention up against a panty, and allowing the adjustable scroll members to receive the panty elastic or fabric of the edge of the panty crotch width into the arcuately shaped adjustable scroll members. The adjustable scroll members receive and hold the panty elastic or panty fabric in position and protect the panty fabric from staining.

Referring now to FIGS. 5 and 6, an absorbent article 10 is shown securely fastened to the crotch portion of the undergarment 40. An undergarment-facing surface 36 of the absorbent article 10 is shown having adjustable scroll member 32 and 34 attached to the undergarment-facing surface 36.

The absorbent pad as used in the absorbent article of the present invention can be formed in the shape of a race track or oval or the like. The absorbent article pad can have other shapes, e.g., such as rectangular shapes other than oval or race track shape, provided that the shapes are designed to cover the pudendal region of a woman. The absorbent pad can be viewed as having a central longitudinal axis X-X. Most absorbent pad articles, such as sanitary napkins and panty liners or shields, are layered in sheets which are longer than they are wide. In addition to the absorbent 14 and the liquid-permeable cover 12, other layers also can be utilized, such as a transfer layer, a layer of anhydrous deodorant material, a layer containing superabsorbent materials, and additional absorbent layers.

The various layers can be vertically stacked, assembled, laminated, and/or bonded together to form the sheet or web of material from which the articles are later cut or stamped out, prior to attachment of the liquid-impermeable baffle of the present invention. The various layers can be bonded together by using heat, pressure, heat and pressure, adhesive, hot melt glue, stitching with thread, ultrasonic bonding, mechanical bonding, thermal bonding, chemical bonding, or a combination of these and/or other means known to those skilled in the art.

The liquid-impermeable baffle 16 can be designed to permit the passage of air or vapor out of the absorbent articles while blocking the passage of body fluid. The liquid-impermeable baffle 16 can be made from any material having these properties. The liquid-impermeable baffle also can be constructed from a material that will block the passage of vapor as well as fluids, if desired. A good material from which the liquid-impermeable baffle 16 can be constructed is a micro-embossed, polymeric film, such as polyethylene or polypropylene. Bi-component films can also be used. A preferred material is polyethylene film. Most preferably, the polyethylene film will have a thickness in the range of from about 0.5 mil to about 2.0 mil.

Construction adhesive can be used in the absorbent articles of the present invention to attach and bond the various layers together. For example, referring to FIG. 2, construction adhesive can be used to bond the liquid-impermeable baffle 16 to the absorbent 14 or to bond the absorbent 14 to the liquid-permeable cover 12. The presence of such construction adhesive and the amount used will depend upon manufacturing specifications. Useful construction adhesives are commercially sold by National Starch and Chemical Company, having an office located at 10 Finderne Ave., Bridgewater, N.J. 08807.

The liquid-permeable cover 12 is designed to contact the body of the wearer and can be constructed of a woven or non-woven material which is easily penetrated by body fluid. The liquid-permeable cover 12 also can be formed from either natural or synthetic fibers. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net materials, also work well. A preferred material is a composite of an apertured thermoplastic film Positioned above a non-woven fabric material. Such a composite material can be formed by extrusion of a polymer onto a web of spunbond material to form an integral sheet. One example of this material is an apertured, thermoplastic polyethylene film bonded to a spunbond material. Spunbond material is a non-woven material which is manufactured and commercially sold by Kimberly-Clark Corporation having an office located at 401 N. Lake Street, Neenah, Wis. 54956. The apertured film/non-woven laminate exhibits a smooth appearance and is soft to the touch. This material is soft and does not irritate the wearer's skin and yet has a cushioned feel because of its bulk. Another material useful as the liquid-permeable cover 12 is a spunbond web of polypropylene. This spunbond web can contain from between about 1 percent to about 6 percent of a whitening agent, such as titanium dioxide ($TiO_2$) or calcium carbonate ($CaCO_3$) to give it a clean, white appearance. A uniform thickness of spunbond is desirable because it will have sufficient strength, after being perforated, to resist being torn or pulled apart during use. The most preferred polypropylene webs have a basis weight of between about 18 grams per square meter ($g/m^2$) to about 40 $g/m^2$. An optimum weight is between about 30 $g/m^2$ to about 40 $g/m^2$.

The absorbent layer 14 can be present as a single layer or as two or more distinct layers. The absorbent layer 14 can be formed from various natural or synthetic fibers such as wood pulp fibers, virgin cellulose fibers, regenerated cellulose fibers, cotton fibers, peat moss, or a blend of pulp and other fibers. The absorbent layer 14 also could be formed from a fine pore fabric such as wet-laid, air-dried tissue or from an uncreped through air-dried (UCTAD) tissue having a basis weight of from about 30 $g/m^2$ to about 120 $g/m^2$. The UCTAD tissue can be prepared by a process disclosed in U.S. Pat. No. 5,048,589 issued to Crook et al. on Sep. 17, 1991. The UCTAD tissue is disclosed in U.S. Pat. No. 5,399,412 issued to Sudall et al. on Mar. 21, 1995. Each of these patents is incorporated by reference and made a part hereof. The absorbent layer 14 also may be comprised of other well-known materials such as cellulose fibers, rayon fibers, cellulose sponge, hydrophilic synthetic sponge, for example polyurethane, and the like.

The absorbent articles 10 also include one or more elongated strips or areas of a garment attachment adhesive 18, for example, referring to FIGS. 2 and 4, secured to the bottom surface of the liquid-permeable baffle 16. The garment attachment adhesive 18 functions to attach the absorbent articles 10 to the inner crotch portion of the undergarment 40 during use. The garment attachment adhesive 18 provides more force in support of the adjustable scroll members 32 and 34 of the present invention to hold the sanitary napkin or panty liner properly aligned and retained relative to the user's vaginal opening so that maximum fluid protection can be obtained. The garment attachment adhesive 18 can cover a portion of the bottom surface of the liquid-impermeable baffle 16. The garment attachment adhesive 18 can consist of a swirl pattern of adhesive or be one or more strips of adhesive or various other patterns. The garment attachment adhesive 18 also can consist of a plurality of adhesive dots which are randomly or uniformly arranged on the exterior surface of the baffle 16. When in strip form, e.g., by way of example, in a single wide strip, the garment attachment adhesive 18 can be aligned along the central longitudinal axis X-X of the absorbent articles 10, respectively. Alternatively, the garment attachment adhesive 18 can be present as two or more spaced apart longitudinal strips. The garment attachment adhesive 18 is of such a nature that it will allow the user to remove the absorbent article 10 and reposition it on her undergarment if needed. A hot melt adhesive which works well as the garment attachment adhesive is commercially sold by National Starch and Chemical Company having an office located at 10 Finderne Avenue, Bridgewater, N.J. 08807.

In order to protect the garment attachment adhesive 18 from contamination or drying prior to use, the adhesive 18 can be protected by a releasable peel strip. The release strip can be a white Kraft paper which is coated on one side so that it can be released from the adhesive 18. The coating can be a silicone coating, such as a silicone polymer commercially available from Akrosil having an office located at 206 Garfield Avenue, Menasha, Wis. 54952. The release strips can be removed by the user prior to attachment of the absorbent articles 10, respectively, to the inner crotch portion of her undergarment 40.

Now, an absorbent article and method have been developed which provide a sanitary napkin or panty liner with side leakage protection, which prevent staining of undergarments and outer garments, and which provide lower cost to produce the absorbent article, with lower manufacturing costs and lower material production costs. The feminine sanitary protection article and method of the present invention provide an accurate placement and a convenient, secure positioning of the absorbent article onto the undergarment. The feminine sanitary protection article and method provide the user with a sense of comfort during use over a variety of situations, including when full absorbency is not needed, yet without sacrificing the full benefits of full leakage protection, convenience of positioning and application, and wearer comfort.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

What is claimed is:

1. An absorbent article, comprising:
   (a) an absorbent having a top sheet surface and an opposite bottom sheet surface, said top sheet surface having a length and a width configured to fit the pudendal region of a woman;
   (b) a liquid-impermeable baffle adjacent to said bottom sheet surface, said baffle having a length and a width covering said bottom sheet surface;
   (c) a pair of garment-attachment adjustable scroll members positioned for receiving a side surface of a crotch portion of an undergarment and for receiving an opposite side surface of said undergarment crotch portion, wherein each said adjustable scroll member comprises an arcuately shaped curled fold on a lateral side surface of said liquid-impermeable baffle; and
   (d) a polyethylene/polypropylene bi-component web sheet material laminated to said liquid-impermeable baffle, wherein said adjustable scroll member comprises an arcuately shaped curled fold on a lateral side surface of said bi-component web sheet material thermal formed to form said curled folds; and
   (e) a liquid impervious backing on said adjustable scroll member.

2. A method of positioning an absorbent article on an undergarment, comprising:
   (a) providing an absorbent configured to fit the pudendal region of a woman;
   (b) positioning a liquid-impermeable baffle on a bottom side of said absorbent;
   (c) providing an adjustable scroll member for receiving a crotch side surface of a crotch portion of an undergarment on a side of said liquid-impermeable baffle to protect said undergarment from side leakage by providing a polyethylene/polypropylene bi-component web sheet material laminated to said liquid-impermeable baffle and forming an arcuately shaped curled fold on a lateral side surface of said bi-component web sheet material;
   (d) receiving said crotch portion into a pair of said adjustable scroll members;
   (e) protecting said crotch portion from side leakage around said absorbent.

3. An absorbent article having side leakage protection and undergarment positioning holders, comprising:
   (a) an absorbent having a top sheet surface and an opposite bottom sheet surface, said top sheet surface having a length and a width configured to fit the pudendal region of a woman;
   (b) a liquid-impermeable baffle adjacent to said bottom sheet surface, said baffle having a length and a width covering said bottom sheet surface;
   (c) a polyethylene/polypropylene bi-component web sheet material laminated to said liquid-impermeable baffle; and
   (d) a pair of garment-attachment adjustable scroll members formed by said bi-component web sheet material for receiving a first arcuately shaped lateral side surface of a crotch portion of an undergarment and for receiving a second arcuately shaped lateral opposite side surface of said undergarment crotch portion opposite said first lateral side surface, wherein said adjustable scroll members comprise arcuately shaped curled folds thermal formed from said bi-component web sheet material on a lateral side surface of said bi-component web sheet material, wherein said garment-attachment adjustable scroll members further comprise a liquid impervious backing.

* * * * *